(12) United States Patent
Theaker et al.

(10) Patent No.: US 12,312,249 B2
(45) Date of Patent: May 27, 2025

(54) GENERATION OF RARE EARTH ELEMENTS FROM ORGANICALLY-ASSOCIATED LEACH SOLUTIONS

(71) Applicant: University of North Dakota, Grand Forks, ND (US)

(72) Inventors: Nolan Theaker, Grand Forks, ND (US); Daniel Laudal, Grand Forks, ND (US); Christine E. Lucky, Madison, WI (US)

(73) Assignee: University of North Dakota, Fargo, ND (US)

( * ) Notice: Subject to any disclaimer, the term of this patent is extended or adjusted under 35 U.S.C. 154(b) by 759 days.

(21) Appl. No.: 17/519,346

(22) Filed: Nov. 4, 2021

(65) Prior Publication Data

US 2022/0144660 A1 May 12, 2022

Related U.S. Application Data

(60) Provisional application No. 63/112,842, filed on Nov. 12, 2020.

(51) Int. Cl.
*C01F 17/10* (2020.01)
*C07C 51/47* (2006.01)
*C22B 3/00* (2006.01)
*C22B 3/04* (2006.01)
*C22B 3/16* (2006.01)
*C22B 59/00* (2006.01)

(52) U.S. Cl.
CPC .............. *C01F 17/10* (2020.01); *C07C 51/47* (2013.01); *C22B 3/00* (2013.01); *C22B 3/04* (2013.01); *C22B 3/16* (2013.01); *C22B 59/00* (2013.01)

(58) Field of Classification Search
None
See application file for complete search history.

(56) References Cited

U.S. PATENT DOCUMENTS

| 9,334,549 | B2 * | 5/2016 | Manepalli | ............... C22B 59/00 |
| 2017/0217802 | A1 * | 8/2017 | Kostedt, IV | .......... C02F 1/5236 |
| 2019/0226055 | A1 * | 7/2019 | Seisenbaeva | ............. B09B 3/00 |

FOREIGN PATENT DOCUMENTS

WO   WO-2020181381 A1 *  9/2020  ............... C22B 3/06

* cited by examiner

*Primary Examiner* — Daniel C. McCracken
*Assistant Examiner* — Joshua Maxwell Speer
(74) *Attorney, Agent, or Firm* — Kinney & Lange, P.A.

(57) ABSTRACT

A method for recovering rare earth elements (REE) from a leach solution. The method includes determining the concentration of a first plurality of contaminates in the leach solution, adding a first amount of oxalic acid to the leach solution and allowing it to react for a first period of time to form a first precipitant and a first liquor, maintaining the pH of the first liquor between 1.5 and 3 by the addition of an alkali base, removing the first precipitant, adding a second amount of oxalic acid to the first liquor and allowing it to react for a second period of time to form a second precipitant and a second liquor, maintaining the pH of the second liquor between 1.5 and 3 by the addition of the alkali base, and removing the second precipitant.

16 Claims, 2 Drawing Sheets

GENERATION OF RARE EARTH ELEMENTS FROM ORGANICALLY-ASSOCIATED LEACH SOLUTIONS

CROSS-REFERENCE TO RELATED APPLICATION(S)

This application claims the benefit of U.S. Provisional Application No. 63/112,842 filed Nov. 12, 2020 for "GENERATION OF RARE EARTH ELEMENTS FROM ORGANICALLY-ASSOCIATED LEACH SOLUTIONS" by N. Theaker, D. Laudal, and C. Lucky.

STATEMENT OF GOVERNMENT INTEREST

This invention was made with government support under DE-FE0027006 awarded by the United States Department of Energy. The government has certain rights in the invention.

BACKGROUND

The present disclosure relates generally to the generation of rare earth elements from organically associated leach solutions. More specifically, this disclosure relates to pH and concentration driven generation of rare earth elements (REE) from organically associated leach solutions.

REE are found in various organically associated materials, but producing individual elements from the ore is expensive and time consuming. Possible extraction methods include electromagnetic separation, flotation process, gravity concentration, hydrometallurgy including ion exchange and solvent extraction, fractional crystallization, and ion exchange. The REE then has to be generated from the leach solution. The cost of REE generation is highly dependent upon the reagents used, quantities thereof, and the purity of the resulting REE. Therefore, it is highly desirable for both cost and environmental reasons to increase the efficiency and selectivity of the REE generation process.

SUMMARY

A method for recovering rare earth elements (REE) from a leach solution. The method includes determining the concentration of a first plurality of contaminates in the leach solution, adding a first amount of oxalic acid to the leach solution and allowing it to react for a first period of time to form a first precipitant and a first liquor, maintaining the pH of the first liquor between 1.5 and 3 by the addition of an alkali base, removing the first precipitant, adding a second amount of oxalic acid to the first liquor and allowing it to react for a second period of time to form a second precipitant and a second liquor, maintaining the pH of the second liquor between 1.5 and 3 by the addition of the alkali base, and removing the second precipitant. The first amount of oxalic acid is between 0.05 mol/L and 0.4 mol/L greater than the concentration of the first plurality of contaminates in the leach solution.

DETAILED DESCRIPTION

Currently REE generation from REE leach solutions is performed by mixing the leach solution with oxalic acid and a base in a single step and allowing the solution to react for a period of time. The resulting product is a mix of REE and other elements. The costs of REE generation are highly dependent upon the reagent/acid utilization during REE generation, the purity achieved following these processes, and hazardous organic waste streams generated. There is also a drive to reduce the environmental impact of the process by decreasing the amount of reagents used. As described herein, the generation is preformed step wise with cumulative additions of oxalic acid to a leaching solution. The pH of the generation process can be controlled by dosing with alkali base. By this method, different molecular weight REEs are recovered in each step, resulting in a product that is purer, and reducing the amount of acid required.

Figure 1:
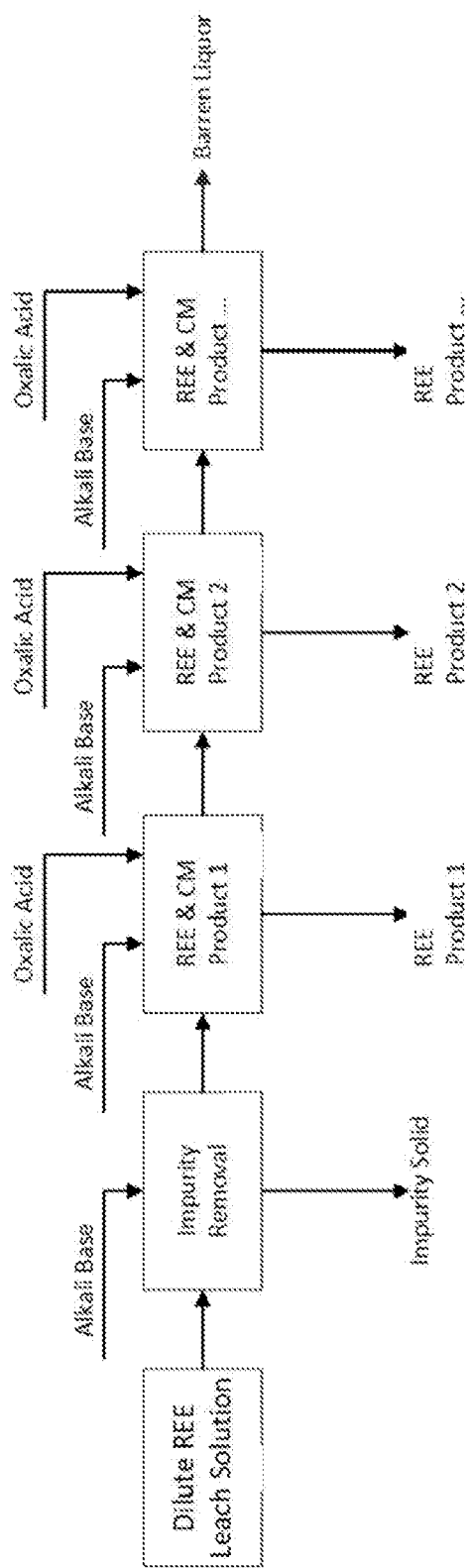
FIG. 1 is a process flow diagram of a representative method for recovering REE from a dilute REE leach solution.

FIG. 1 is a process flow diagram of a representative method for recovering REE from a dilute REE leach solution. FIG. 1 shows dilute REE leach solution 102 is treated with an alkali base in impurity removal stage 104. The impurity solids are removed. The remaining liquor is treated with an alkali base and oxalic acid in first product stage 106, resulting in a first REE product precipitating out of the liquor. The first REE product is removed. The remaining liquor is treated with an alkali base and oxalic acid in second product stage 108, resulting in a second REE product precipitating out of the liquor. The second REE product is removed. The remaining liquor is treated with an alkali base and oxalic acid in third product stage 110, resulting in a third REE product precipitating out of the liquor. The third REE product is removed. The barren liquor is then further processed or disposed of as waste. The various REE products are further refined.

Dilute REE leach solution 102 is a solution from an REE extraction process containing REE and other elements and/or minerals. The solution can be aqueous. REE leach solution 102 has a number of impurities. Some initial impurities are removed in impurity removal stage 104. These impurities, which are removed in some quantity, can be, for example, iron or vanadium. Impurity removal stage 104 comprises adding an alkali base to REE leach solution 102 and allowing it to react for a period of time. The alkali base can be, for example, sodium carbonate, sodium hydroxide, potassium carbonate, potassium hydroxide, or a combination thereof. The alkali base can be added in a concentration to give the solution a desired pH. For example, the alkali base can be added such that the pH of the solution is between 1.5 and 3, between 1.75 and 2.75 or between 2 and 2.5. The pH, total suspended solids density, or a combination thereof can be monitored continuously. The alkali base can be in powder form or can be in solution. Impurity removal stage 104 is allowed to proceed for a period of time, for example 1 to 12 hours, 3 to 10 hours, or 5 to 7 hours. The impurities precipitate out of the solution and are removed by an acceptable method, for example filtration, vacuum filtration, centrifuge, or decanting. The resulting liquor is then treated in first product step 106.

In first product step 106, the concentration of a first set of contaminants is determined through, for example, through off-line liquid analysis or through determining the total suspended solids density. The first set of contaminants can be, for example, iron, aluminum, vanadium, or a combination thereof. Then, oxalic acid is added to the mixture. Oxalic acid can be added as a powder or as a solution. The concentration of oxalic acid in the mixture is, for example, between 0.05 M and 0.6 M, between 0.075 M and 0.5 M, or 0.1 M and 0.4 M. In some embodiments the concentration of oxalic acid above the concentration of the first set of contaminants in the liquor is, for example, between 0.25 M and 0.17 M, between 0.5 M and 0.16 M, or between 0.75 M and 0.15 M. The mixture is continuously monitored for pH, for example, by a flow past or submerged pH meter. An alkali base is added to the mixture to maintain the pH in a desired range, for example, between 1.5 and 3, between 1.75 and 2.75, or between 2.0 and 2.5. The alkali base can be, for example, sodium carbonate, sodium hydroxide, potassium carbonate, potassium hydroxide, or a combination thereof. The alkali can be a powder or solution. The mixture is allowed to react for a period of time, for example, 30 minutes to 3 hours, 1 hour to 2.5 hours, or 1.5 to 2 hours. The resulting slurry of particles is measured for the slurry density to specific targets, such as 0.001% to 5.0% by weight solids through use of a total suspended solids sensor. Based upon the results of this sensor, additional oxalic acid may be fed to reach a target value. The first REE product precipitates out of solution and is removed by an acceptable method, for example filtration, vacuum filtration, centrifuge, or decanting. The first REE product can comprise, for example, europium, gadolinium, or a combination thereof. The remaining liquor is then treated in second product step 108.

In second product step 108, the concentration of a second set of contaminants is determined through, for example, through off-line liquid analysis, online spectrographic methods, or some combination thereof. The second set of contaminants can be, for example, calcium, magnesium, or a combination thereof. Then oxalic acid is added to the mixture. Oxalic acid can be added as a powder or as a solution. The concentration of oxalic acid in the mixture is, for example, between 0.125 M and 0.75 M, between 0.15 M and 0.65 M, or 0.175 M and 0.55 M. In some embodiments the concentration is between 0.25 M and 0.17 M, between 0.5 M and 0.16 M, or between 0.75 M and 0.15 M greater than the concentration of the oxalic acid in the previous stage. The mixture is continuously monitored for pH, for example, by flow past or submerged pH meter. An alkali base is added to the mixture to maintain the pH in a desired range, for example, between 1.5 and 3, between 1.75 and 2.75, or between 2.0 and 2.5. The alkali base can be, for example, sodium carbonate, sodium hydroxide, potassium carbonate, potassium hydroxide, or a combination thereof. The alkali can be a powder or solution. The mixture is allowed to react for a period of time, for example, 30 minutes to 3 hours, 1 hour to 2.5 hours, or 1.5 to 2 hours. The second REE product precipitates out of solution and is removed by an acceptable method, for example filtration, vacuum filtration, centrifuge, or decanting. The resulting slurry of particles is measured for the slurry density to specific targets, such as 0.01% to 20.0% by weight solids through use of a total suspended solids sensor. Based upon the results of this sensor, additional oxalic acid may be fed to reach a target value. The second REE product can comprise, for example, ytterbium, cerium, or a combination thereof. The remaining liquor is then treated in third product step 110.

In third product step 110, a small amount oxalic acid is added to the mixture. In some embodiments the amount of oxalic acid added is for example, no greater than 0.2 M, no greater than 0.15, or no greater than 0.1 M. Oxalic acid can be added as a powder or as a solution. The mixture is continuously monitored for pH, for example, by flow past or submerged pH meter. An alkali base is added to the mixture to maintain the pH in a desired range, for example, between 1.5 and 3, between 1.75 and 2.75, or between 2.0 and 2.5. The alkali base can be, for example, sodium carbonate, sodium hydroxide, potassium carbonate, potassium hydroxide, or a combination thereof. The alkali can be a powder or solution. The mixture is allowed to react for a period of time, for example, 30 minutes to 3 hours, 1 hour to 2.5 hours, or 1.5 to 2 hours. The third REE product precipitates out of solution and is removed by an acceptable method, for example filtration, vacuum filtration, centrifuge, or decanting. The resulting slurry of particles is measured for the slurry density to specific targets, such as 0.001% to 5.0% by weight solids through use of a total suspended solids sensor. Based upon the results of this sensor, additional oxalic acid may be fed to reach a target value. The third REE product can comprise, for example, scandium, cobalt, gallium, or a combination thereof. The remaining liquor is then further treated or disposed of.

EXAMPLES

Example 1—Multiple Solid REE Extraction

The process utilized in example 1 for preliminary REE separation and the generation of multiple solid REE products from the pregnant leach solution involves the piecewise addition of oxalic acid and sodium carbonate to the REE-bearing liquid. The concentration of iron and aluminum is determined on-line with spectral analyzers or through rigorous sampling. Oxalate complexes with iron and aluminum, and will deprive the REE of this anion. For each mole of Fe or Al present in the liquid as an ion (not a solid), 1.5 moles of oxalate must be added to counteract, in addition to the 0.05-0.1 mole/L addition to facilitate REE precipitation. Then a concentration of oxalic acid equal to the 0.05-0.1 moles/L greater than the equimolar concentration of the iron and aluminum is added to the liquid via screwfeeder and/or auger, and the pH is controlled to a pH of between 1 and 3 using continuous feed of the sodium carbonate on a programmable logic controller feedback loop. The mixture is stirred at a low stir rate to permit crystal growth and may be seeded with previously generated REE solids to improve the kinetics and/or selectivity. This stirring occurs for at least 1.5 hours if no seed crystals are present, or as little as 30 minutes with seed crystals. The resulting solution and the solids contained are filtered via any method (centrifuge, vacuum, or pressure), and washed of the residual solution with water.

The solution is then added to a separate tank, in which additional oxalate, typically 0.05-0.15 M, is added, and the pH controlled in a similar fashion as to the previous step. Each solid is then filtered in series as produced.

Figure 2A:
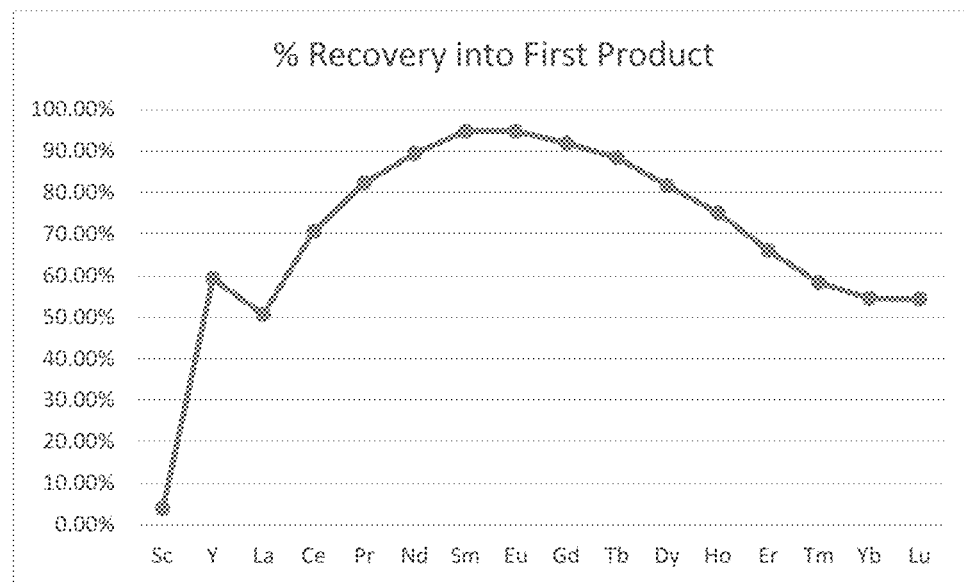
FIG. 2A is a graph of the experimental element distribution of the first REE product after extraction.
Figure 2B:
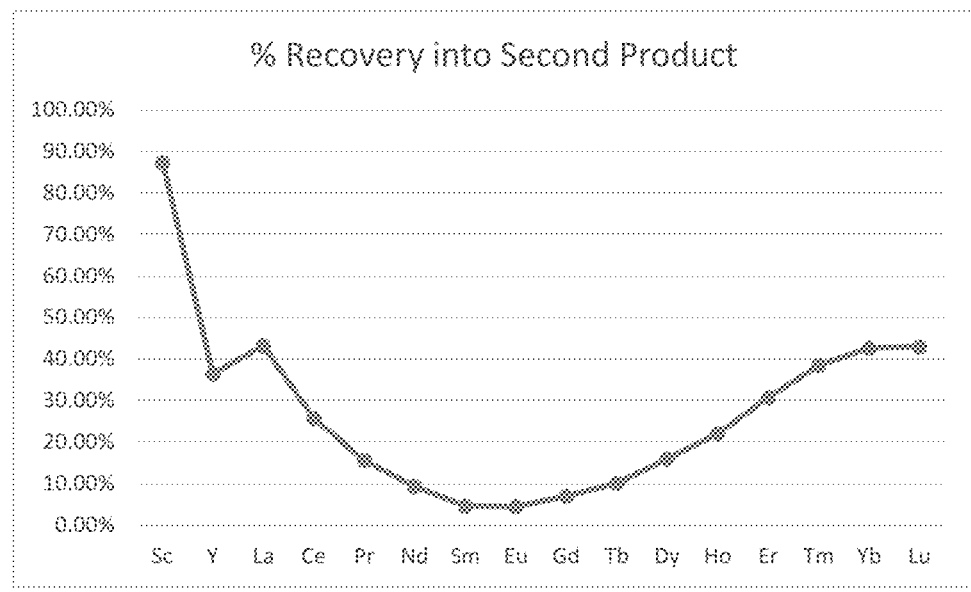
FIG. 2B is a graph of the experimental element distribution of the second REE product after extraction.

FIG. 2A is a graph of the element distribution of the REE product in the first extraction product after experiment extractions described herein. FIG. 2A is a graph of the element distribution of the REE product in the first extraction product after experiment extractions described herein. FIG. 2B is a graph of the element distribution of the REE product in the second extraction product after experimental extractions described herein. The composition of the first REE product can be a bell curve of the lanthanum series centered on europium and gadolinium. Very little if any of the high and low molecular weight lanthanides are present in the first REE product. The composition of the second REE product can be a mirror of the bell curve of the first REE product. Very little, if any, of the middle molecular weight lanthanides are present in the second REE product.

DISCUSSION OF POSSIBLE EMBODIMENTS (This section is another restatement of the claims, and will be finished after the claims have been finalized.)

The following are non-exclusive descriptions of possible embodiments of the present invention.

A method for recovering rare earth elements (REE) from a leach solution, the method comprising: determining the concentration of a first plurality of contaminates in the leach solution, adding a first amount of oxalic acid to the leach solution and allowing it to react for a first period of time to form a first precipitant and a first liquor, maintaining the pH of the first liquor between 1.5 and 3 by the addition of an alkali base, removing the first precipitant, adding a second amount of oxalic acid to the first liquor and allowing it to react for a second period of time to form a second precipitant and a second liquor, maintaining the pH of the second liquor between 1.5 and 3 by the addition of the alkali base, and removing the second precipitant, wherein the first amount of oxalic acid is between 0.05 mol/L and 0.4 mol/L greater than concentration of the first plurality of contaminates in the leach solution.

The method of the preceding paragraph can optionally include, additionally and/or alternatively, any one or more of the following features, configurations and/or additional components:

A further embodiment of the foregoing method further comprising the steps of: adding a third amount of oxalic acid to the second liquor and allowing it to react for a third period of time to form a third precipitant and a third liquor, maintaining the pH of the third liquor between 1.5 and 3 by the addition of the alkali base, and removing the third precipitant.

A further embodiment of any of the foregoing methods wherein the first plurality of contaminates comprises iron, aluminum, vanadium, or a combination thereof.

A further embodiment of any of the foregoing methods wherein the first precipitant comprises europium, gadolinium, or a combination thereof.

A further embodiment of any of the foregoing methods further comprising the step of determining the concentration of a second plurality of contaminates in the leach solution, wherein the second amount of oxalic acid is between 0.05 mol/L and 0.4 mol/L greater than the concentration of the second plurality of contaminates in the leach solution.

A further embodiment of any of the foregoing methods wherein the second plurality of contaminates comprises calcium, magnesium, or a combination thereof.

A further embodiment of any of the foregoing methods wherein the second precipitant comprises ytterbium, cerium, or a combination thereof.

A further embodiment of any of the foregoing methods wherein the third amount of oxalic acid is less than 0.2 mol/L.

A further embodiment of any of the foregoing methods wherein the third precipitant comprises scandium, cobalt, gallium, or a combination thereof.

A further embodiment of any of the foregoing methods wherein the alkali base comprises sodium carbonate, sodium hydroxide, potassium carbonate, potassium hydroxide, or a combination thereof.

A further embodiment of any of the foregoing methods wherein the alkali base is a powder.

A further embodiment of any of the foregoing methods wherein the oxalic acid is a powder.

A further embodiment of any of the foregoing methods wherein the first period of time is between 1 hour and 12 hours.

A further embodiment of any of the foregoing methods wherein the second period of time is between 30 minutes and 3 hours.

A further embodiment of any of the foregoing methods wherein the third period of time is between 30 minutes and 3 hours. A further embodiment of any of the foregoing methods wherein the leach solution has a total suspended solids density, and wherein the step of determining the concentration of a first plurality of contaminates in the leach solutions comprises measuring the total suspended solids density.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A method for recovering rare earth elements (REE) from a leach solution, the method comprising:
    determining a total concentration of a first plurality of contaminates present in the leach solution, the first plurality of contaminates comprising iron, aluminum, vanadium, or a combination thereof, and including any iron, aluminum, and vanadium present in the leach solution,
    adding a first amount of oxalic acid to the leach solution and allowing it to react for a first period of time to form a first precipitant and a first liquor,
    maintaining the pH of the first liquor between 1.5 and 3 by the addition of an alkali base,
    removing the first precipitant,
    adding a second amount of oxalic acid to the first liquor and allowing it to react for a second period of time to form a second precipitant and a second liquor,
    maintaining the pH of the second liquor between 1.5 and 3 by the addition of the alkali base, and
    removing the second precipitant,
    wherein the first amount of oxalic acid is between 0.05 mol/L and 0.4 mol/L greater than the total concentration of the first plurality of contaminates in the leach solution.

2. The method of claim 1, further comprising the steps of:
    adding a third amount of oxalic acid to the second liquor and allowing it to react for a third period of time to form a third precipitant and a third liquor,
    maintaining the pH of the third liquor between 1.5 and 3 by the addition of the alkali base, and
    removing the third precipitant.

3. The method of claim 2 wherein the third amount of oxalic acid is less than 0.2 mol/L.

4. The method of claim 2 wherein the third precipitant comprises scandium, cobalt, gallium, or a combination thereof.

5. The method of claim 2 wherein the third period of time is between 30 minutes to 3 hours.

6. The method of claim 1 wherein the first precipitant comprises europium, gadolinium, or a combination thereof.

7. The method of claim 1 further comprising the step of determining the concentration of a second plurality of contaminates in the leach solution, wherein the second amount of oxalic acid is between 0.05 mol/L and 0.4 mol/L greater than the concentration of the second plurality of contaminates in the leach solution.

8. The method of claim 7 wherein the second plurality of contaminates comprises calcium, magnesium, or a combination thereof.

9. The method of claim 7 wherein the second precipitant comprises ytterbium, cerium, or a combination thereof.

10. The method of claim 1 wherein the pH of the first liquor is continuously monitored.

11. The method of claim 1 wherein the alkali base comprises sodium carbonate, sodium hydroxide, potassium carbonate, potassium hydroxide, or a combination thereof.

12. The method of claim 11 wherein the alkali base is a powder.

13. The method of claim 1 wherein the oxalic acid is a powder.

14. The method of claim 1 wherein the first period of time is between 1 hour and 12 hours.

15. The method of claim 1 wherein the second period of time is between 30 minutes to 3 hours.

16. The method of claim 1 wherein the leach solution has a total suspended solids density, and wherein the step of determining the concentration of a first plurality of contaminates in the leach solutions comprises measuring the total suspended solids density.

* * * * *